United States Patent [19]

Camenzind

[11] Patent Number: 5,629,422
[45] Date of Patent: May 13, 1997

[54] (DI)ARYLAMINOALKYL 4-HYDROXYPHENYLALKANECARBOXYLATES

[75] Inventor: Hugo Camenzind, Bern, Switzerland

[73] Assignee: Ciba Geigy Corporation, Tarrytown, N.Y.

[21] Appl. No.: 343,393

[22] Filed: Nov. 22, 1994

[30] Foreign Application Priority Data

Nov. 29, 1993 [CH] Switzerland .................. 3558/93

[51] Int. Cl.$^6$ .................. C07D 279/22; C07D 221/02; C07C 69/76
[52] U.S. Cl. .................. 544/38; 546/112; 560/75
[58] Field of Search .................. 560/75; 544/38; 546/112

[56] References Cited

U.S. PATENT DOCUMENTS

| | | | |
|---|---|---|---|
| 2,962,531 | 11/1960 | Coffield | 260/570.9 |
| 3,119,871 | 1/1964 | Boag et al. | 260/570 |
| 3,224,974 | 12/1965 | Boag et al. | |
| 3,225,099 | 12/1965 | Coffield | 260/570.9 |
| 3,435,065 | 3/1969 | Dexter et al. | 560/75 |
| 3,441,575 | 4/1969 | Dexter et al. | 560/75 |
| 3,457,286 | 7/1969 | Dexter et al. | 260/404 |
| 3,873,459 | 3/1975 | Pawlak et al. | 252/51.5 |
| 3,920,729 | 11/1975 | Sagawa et al. | 560/75 |
| 3,984,460 | 10/1976 | Spivack | 560/75 |
| 4,448,969 | 5/1984 | Ramey et al. | 548/301 |
| 4,877,824 | 10/1989 | Evans | 524/83 |
| 5,089,656 | 2/1992 | Yu | 560/75 |

FOREIGN PATENT DOCUMENTS

| | | |
|---|---|---|
| 1246067 | 12/1988 | Canada . |
| 2051156 | 3/1992 | Canada . |
| 0119160 | 9/1984 | European Pat. Off. . |
| 286595 | 10/1988 | European Pat. Off. . |
| 3426367 | 1/1986 | Germany . |

OTHER PUBLICATIONS

P. Klemchuck, Ullman's Encyclopedia of Industrial Chemistry, 5th Ed. vol. A3 (1985) pp. 91–111.

*Primary Examiner*—Kriellion S. Morgan
*Attorney, Agent, or Firm*—Michele A. Kovaleski; David R. Crichton

[57] ABSTRACT

New compounds of the formula I are described which are active, for example, as antioxidants, and also a process for their preparation:

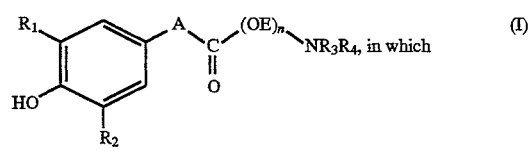

$R_1$ and $R_2$ are independently of one another $C_1$-$C_{20}$alkyl, allyl, methallyl, unsubstituted or $C_1$-$C_8$alkyl-substituted $C_5$-$C_{12}$cycloalkyl, $C_5$-$C_8$cycloalkenyl, phenyl or $C_7$-$C_9$phenylalkyl, A is a direct bond, —CH$_2$—, —(CH$_2$)$_2$— or —CH$_2$—CH(CH$_3$)—, E is —(CH$_2$)$_2$—, —CHR$_6$—CH$_2$— or —CH$_2$CHR$_6$—, n is 1, 2 or 3, $R_3$ is $C_1$-$C_{18}$alkyl or is $C_1$-$C_{18}$alkyl which is interrupted by —O— or —S—, unsubstituted or $C_1$-$C_8$alkyl-substituted $C_5$-$C_{12}$cycloalkyl, phenyl, naphthyl, $C_7$-$C_9$phenylalkyl, $C_7$-$C_{18}$alkylphenyl or is of the formula

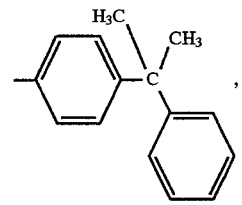

$R_4$ is phenyl, naphthyl, $C_7$-$C_9$phenylalkyl, $C_7$-$C_{18}$alkylphenyl or is a radical of the formula

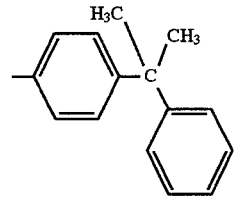

or
NR$_3$R$_4$ is a group of the formula

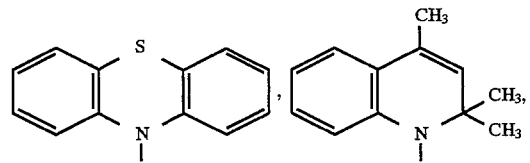

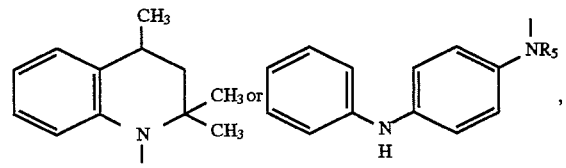

$R_5$ is hydrogen, $C_1$-$C_{18}$alkyl, allyl, methallyl, unsubstituted or $C_1$-$C_8$alkyl-substituted $C_5$-$C_{12}$cycloalkyl, phenyl or naphthyl, $R_6$ is hydrogen, $C_1$-$C_{20}$alkyl or $C_2$-$C_{20}$alkyl which is interrupted by —O—, —S—, —NR$_7$— or —C(O)O—, and $R_7$ is hydrogen or $C_1$-$C_6$alkyl.

4 Claims, No Drawings

(DI)ARYLAMINOALKYL 4-HYDROXYPHENYLALKANECARBOXYLATES

The present invention relates to novel esters of 4-hydroxyphenylcarboxylic acids, which are suitable for stabilizing organic material, to compositions comprising them, to a process for their preparation and to their use as stabilizers.

It is known to add stabilizers to organic substances in order to prevent the degradation of the latter by electromagnetic waves, chemicals or heat. For a long time now use has been made in this field of the sterically hindered phenols and the aromatic amines (cf. Ullmann's Encyclopedia of Industrial Chemistry, 5th Ed. Vol. A3 (1985) pp. 99–111, "Antioxidants").

In the meantime antioxidants have also been disclosed which combine amine and phenol function in one molecule (cf. EP-A-0 119 160, U.S. Pat. Nos. 3,225,099, 2,962,531, 3,119,871 and 3,224,974).

Such antioxidants can likewise be employed in lubricants, for example engine oils, where their function is in particular to prevent deposits of sludge (deposit control), which may considerably reduce the service life of combustion engines.

It has now surprisingly been found that substances which include phenolic and aminic groups connected in a certain way are particularly well suited as stabilizers, especially for lubricants.

The invention therefore relates to compounds of the formula I

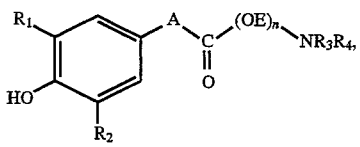

in which

R$_1$ and R$_2$ are independently of one another C$_1$–C$_{20}$alkyl, allyl, methallyl, unsubstituted or C$_1$–C$_8$alkyl-substituted C$_5$–C$_{12}$cycloalkyl, C$_5$–C$_8$cycloalkenyl, phenyl or C$_7$–C$_9$phenylalkyl, A is a direct bond, —CH$_2$—, —(CH$_2$)$_2$— or —CH$_2$—CH(CH$_3$)—, E is —(CH$_2$)$_2$—, —CHR$_6$—CH$_2$— or —CH$_2$CHR$_6$—, n is 1, 2 or 3, R$_3$ is C$_1$–C$_{18}$alkyl or is C$_2$–C$_{18}$alkyl which is interrupted by —O— or —S—, unsubstituted or C$_1$–C$_8$alkyl-substituted C$_5$–C$_{12}$cycloalkyl, phenyl, naphthyl, C$_7$–C$_9$phenylalkyl, C$_7$–C$_{18}$alkylphenyl or is of the formula

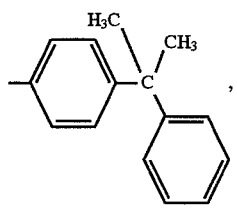

R$_4$ is phenyl, naphthyl, C$_7$–C$_9$phenylalkyl, C$_7$–C$_{18}$alkylphenyl or is a radical of the formula

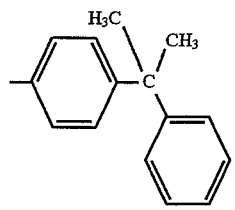

or

NR$_3$R$_4$ is a group of the formula

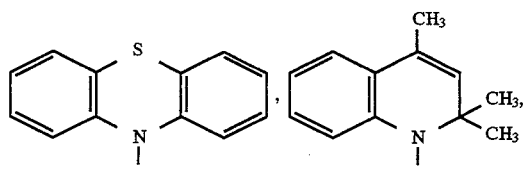

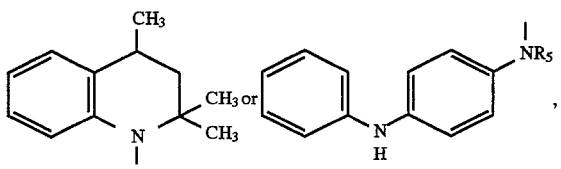

R$_5$ is hydrogen, C$_1$–C$_{18}$alkyl, allyl, methallyl, unsubstituted or C$_1$–C$_8$alkyl-substituted C$_5$–C$_{12}$cycloalkyl, phenyl or naphthyl, R$_6$ is hydrogen, C$_1$–C$_{20}$alkyl or C$_2$–C$_{20}$alkyl which is interrupted by —O—, —S—, —NR$_7$— or —C(O)O—, and R$_7$ is hydrogen or C$_1$–C$_6$alkyl.

R$_1$, R$_2$, R$_3$, R$_5$ and R$_6$ as C$_1$–C$_{18}$alkyl or C$_1$–C$_{20}$alkyl, respectively, may be straight-chain or branched and are for example methyl, ethyl, propyl, isopropyl, n-butyl, isobutyl, t-butyl, pentyl, isopentyl, hexyl, heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl, 1-methylundecyl and additionally, for example, eicosyl. Where these radicals are groups with a lower number of carbon atoms, corresponding examples are likewise to be taken from the above list. This applies also to R$_7$ and to R$_8$, which is introduced below for formula III. The alkyl radicals mentioned preferably have 1–12 carbon atoms, especially 1–6 carbon atoms and in particular 1–4 carbon atoms.

R$_1$, R$_2$, R$_4$ and R$_3$ as C$_7$–C$_9$phenylalkyl are for example benzyl, 1— or 2-phenylethyl, 3-phenylpropyl, α,α-dimethylbenzyl or 2-phenylisopropyl, but preferably benzyl.

R$_4$ and R$_3$ as C$_7$–C$_{18}$alkylphenyl may contain linear or branched alkyl groups, it being advantageous for 1–3, especially 1 or 2, alkyl groups to be present. Examples are tolyl, the isomeric xylyls, ethylphenyl, isopropylphenyl, tert-butylphenyl, sec-pentylphenyl, n-hexylphenyl, tert-octylphenyl, isononylphenyl and n-dodecylphenyl.

Examples of the abovementioned unsubstituted or C$_1$–C$_8$alkyl-substituted cycloalkyl groups of 5–12 carbon atoms (those having 5–8 carbon atoms, especially 5 or 6 carbon atoms are preferred) are cyclopentyl, cyclohexyl, cyclooctyl, cyclododecyl, 2- or 4-methylcyclohexyl, dimethylcyclohexyl, trimethylcyclohexyl and t-butylcyclohexyl, with cyclohexyl being particularly preferred.

$C_5$–$C_8$Cycloalkenyl radicals differ from the above-described cycloalkyl radicals only by a >C═C< double bond in the ring. As $C_5$–$C_8$cycloalkenyl $R_1$ and $R_2$ are preferably cyclopentenyl and cyclohexenyl.

In the abovementioned interrupted alkyl radicals ($R_3$ and $R_6$), the interrupting atom or the interrupting group is located within the carbon chain, which may be interrupted one or more times. Interruption is preferably by only one member of the group —O—, —S—, —$NR_7$— and —CO—O—. Where $R_3$ and $R_6$ are interrupted by oxygen or sulfur they contain, for example, structural units such as —$CH_2CH_2$—O—$CH_2CH_2$—, —$CH_2CH_2$—S—$CH_2CH_2$—, or —O—$(CH_2)_6$—O—. The units (O—$CH_2$—$CH_2$) and (S—$CH_2CH_2$) may in particular also occur two or more times adjacent to one another. Examples of radicals interrupted by —O— or —S— are $CH_3$—O—$CH_2$—, $CH_3$—S—$CH_2$—, $CH_3$—O—$CH_2CH_2$—O—$CH_2$—, $CH_3$—(O—$CH_2CH_2$—)$_2$O—$CH_2$—, $CH_3$—(O—$CH_2CH_2$—)$_3$O—$CH_2$— oder $CH_3$—(O—$CH_2CH_2$—)$_4$O—$CH_2$—. $C_2$–$C_{20}$alkyl interrupted by >$NR_7$ is for example $CH_3$—NH—$CH_2$— or $CH_3$—N($CH_3$)—$CH_2$—.

$C_2$–$C_{20}$Alkyl interrupted by —CO—O— is for example $CH_3$—CO—O—$CH_2$— or $C_1$–$C_{18}$alkyl—CO—O—$CH_2CH_2$—.

$R_6$ as uninterrupted alkyl is preferably $C_1$–$C_{17}$alkyl, for example $C_1$–$C_4$alkyl, and especially methyl.

The invention also relates to mixtures of compounds of the formula I with different indices n, especially those mixtures as are obtainable from the process described below.

The index n is preferably 1 or 2, especially 1.

Preferred compounds of the formula I are those in which $R_1$ and $R_2$ are independently of one another $C_1$–$C_8$alkyl, $C_5$–$C_8$cycloalkyl or $C_7$–$C_9$phenylalkyl, A is —$(CH_2)_2$— or —$CH_2$—CH($CH_3$)—, E is —$(CH_2)_2$—, —$CHR_6$—$CH_2$— or —$CH_2CHR_6$—, n is 1 or 2, $R_3$ and $R_4$ are independently of one another phenyl, naphthyl, $C_7$–$C_9$phenylalkyl or $C_7$–$C_{18}$alkylphenyl, or $NR_3R_4$ is a group of the formula

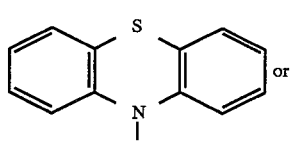

or

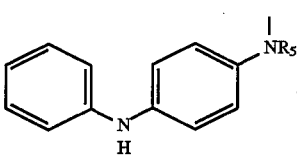

, $R_5$ is hydrogen, $C_1$–$C_8$alkyl or phenyl, and $R_6$ is hydrogen, $C_1$–$C_{20}$alkyl or $C_2$–$C_{20}$alkyl which is interrupted by —O— or —S—.

Particularly preferred compounds of the formula I are those in which $R_1$ and $R_2$ independently of one another are $C_1$–$C_5$alkyl, $C_5$–$C_6$cycloalkyl or $C_7$–$C_9$phenylalkyl, n is 1 or 2, A is —$(CH_2)_2$— or —$CH_2$—CH($CH_3$)—, E is —$(CH_2)_2$—, —$CHR_6$—$CH_2$— or —$CH_2CHR_6$—, $R_3$ and $R_4$ are independently of one another phenyl, naphthyl, $C_7$–$C_9$phenylalkyl or $C_7$–$C_{18}$alkylphenyl, or $NR_3R_4$ is a group of the formula

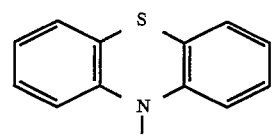

and $R_6$ is hydrogen or $C_1$–$C_4$alkyl.

The compounds of the formula I are outstandingly suitable for stabilizing organic materials against light-induced, thermal and/or oxidative degradation. The invention therefore also relates to compositions comprising an organic material which is sensitive to such degradation reactions and at least one compound of the formula I, and, respectively, to the use of compounds of the formula I and stabilizers for organic materials to counter the abovementioned types of degradation.

The compounds of the formula I may in particular be employed as stabilizers for natural, semisynthetic or synthetic polymers, especially thermoplastics and elastomers, and for functional fluids, especially lubricants and hydraulic fluids. Examples of such substrates can be taken from the following listing of suitable materials.

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer, and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crossing agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblencls), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

In the compositions according to the invention the compounds of the formula I are advantageously present to the extent of from 0.01 to 10% by weight, for example from 0.05 to 5% by weight, preferably from 0.05 to 3% by weight but in particular from 0.1 to 2% by weight. This content may involve one or more of these compounds of the formula I, and the percentages by weight relate to the overall quantity of these compounds. The basis for this calculation is the overall weight of the organic material without the compounds of the formula I.

Incorporation into the materials can be effected, for example, by mixing or by applying the compounds of the formula I and, if desired, further additives by methods which are conventional in the art. Where polymers are involved, especially synthetic polymers, incorporation may be effected before or during the shaping operation, or by applying the dissolved or dispersed compounds to the polymer, if desired with subsequent evaporation of the solvent. In the case of elastomers these may also be stabilized as latices. A further possibility for incorporating the compounds of the formula I into polymers consists in their addition before, during or directly after the polymerization of the corresponding monomers and/or prior to crosslinking. In this context the compounds of the formula I can be added as such or else in encapsulated form (e.g. in waxes, oils or polymers). In the case of addition before or during the polymerization the compounds of the formula I may also act as regulators of the chain length of the polymers (chain terminators).

The compounds of the formula I or mixtures thereof can also be added to the plastics to be stabilized in the form of a masterbatch which contains these compounds, for example, in a concentration of from 2.5 to 25% by weight.

The compounds of the formula I can advantageously be incorporated by the following methods:

as emulsion or dispersion (e.g. to latices or emulsion polymers)

as a dry mixture during the mixing of additional components or polymer mixtures by direct addition to the processing apparatus (e.g. extruder, internal mixer etc.)

a solution or melt.

Polymer compositions according to the invention may be used in various forms or processed to give various products, for example as or to films, fibres, strips, moulding compositions and profiles, or as binders for surface coatings, adhesives or putties.

The invention also relates to a process for stabilizing organic material, especially thermoplastic polymers, elastomers or functional fluids, in particular lubricants, against oxidalive, thermal and/or light-induced degradation, which comprises adding or applying to this material, as stabilizers, compounds of the formula I.

The compounds of the formula I are particularly suitable, for example, for imparting improved service properties to functional fluids. In this context reference should be made in particular to their surprisingly good antioxidative and sludge-preventing (deposit control) action. Therefore the invention also includes compositions comprising a functional fluid and at least one compound of the general formula I, as described above.

Examples of functional fluids which can be mentioned are lubricants, hydraulic fluids and metalworking fluids. In this document the term functional fluids is intended to include lubricating greases.

The lubricants in question are based, for example, on mineral or synthetic oils or mixtures thereof or on vegetable and animal oils, fats and waxes. The lubricants are familiar to the person skilled in the art and are described in the relevant technical literature, for example in Dieter Klamann, "Schmierstoffe und verwandte Produkte" [Lubricants and related products] (Verlag Chemie, Weinheim, 1982), in Schewe-Kobek, "Das Schmiermittel-Taschenbuch" [The Lubricant Handbook] (Dr. Alfred Hüthig-Verlag, Heidelberg, 1974) and in "Ullmanns Enzyklopädie der technischen Chemie" [Ullmann's Encyclopedia of Industrial Chemistry], Vol. 13, pages 85–94 (Verlag Chemie, Weinheim, 1977).

The lubricants are in particular oils and fats based, for example, on a mineral oil. Oils are preferred.

The mineral oils are based in particular on hydrocarbon compounds.

Examples of synthetic lubricants include lubricants based on aliphatic or aromatic carboxyl esters, polymeric esters, polyalkylene oxides, phosphoric esters, poly-$\alpha$-olefins or silicones, a diester of a dibasic acid with a monohydric alcohol, for example dioctyl sebacate or dinonyl adipate, a triester of trimethylolpropane with a monobasic acid or a mixture of such acids, for example trimethylolpropane tripelargonate, trimethylolpropane tricaprylate or mixtures thereof, a tetraester of pentaerythritol with a monobasic acid or a mixture of such acids, for example pentaerythritol tetracaprylate, or a complex ester of monobasic and dibasic acids with polyhydric alcohols, for example a complex ester of trimethylolpropane with caprylic and sebacic acid or of a mixture thereof. Particularly suitable examples besides mineral oils are poly-$\alpha$-olefins, ester-based lubricants, phosphates, glycols, polyglycols and polyalkylene glycols, and mixtures thereof with water.

Plant-based lubricants which can be mentioned are the oils, fats and waxes obtained, for example, from olives, palms, palm kernels, beet, oilseed rape, linen, nuts, soya, cotton, Ricinus, sunflower, seeds of Cucurbitaceae, coconut, corn or modified forms thereof, for example sulfurized or epoxidized oils such as epoxidized soya oil, and mixtures of the substances. Examples of animal oils, fats and waxes which can be employed as lubricants are tallows, fish oils, sperm oil, neat's foot oil, train oils and lard oils, and modified forms and mixtures thereof.

Metalworking fluids such as rolling, drawing and cutting oils are mostly based on the above-described mineral oils and synthetic oils and may also be present as oil-in-water or water-in-oil emulsions. The same applies to hydraulic fluids. Other functional fluids which enter into consideration are, for example, compressor oils and spinning preparations.

The compounds of the formula I as described above may be present in the functional fluid, for example, in quantities of from 0.01 to 10% by weight, advantageously in quantities of from 0.05 to 5% by weight, preferably in a quantity of from 0.05 to 3% by weight and very especially from 0.5 to 1.5% by weight, based on the composition.

The compounds of the formula I may be admixed with the functional fluid in a manner known per se. The compounds are, for example, readily soluble in oils. It is also possible to prepaxe a so-called masterbatch which depending on the use can be diluted with the corresponding functional fluid to application concentrations.

In addition to the compounds and mixtures according to the invention the compositions according to the invention, especially when they contain organic, preferably synthetic, polymers, may also contain other conventional additives. Examples of such additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example $\alpha$-tocopherol, $\beta$-tocopherol, $\gamma$-tocopherol, $\delta$-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenyl], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methhylbenzyl)-6-tert-butyl-4-methylphenyl]terephthalate, 1,1-bis-(3,5-dimethyl-2-hydroxyphenyl)butan, 2,2-bis-(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra-(5-tertbutyl-4-hydroxy-2-methylphenyl)pentane.

1.7. O—, N— and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tertbutyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malohate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocycnate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, uiethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexy-1-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis (3,5-di-tert-butyl-4-hydroxyphenylpropionyl) trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$―]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis (4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,62-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetraearboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis (4-n-butyl-amino-2,2,6,6-tetramethylpiperdidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperdidyl)pyrrolidin-2,5-dione, 3-dodecyl-1-(1,2,2,6,6-pentamethyl-4-piperdidyl) pyrrolidine-2,5-dione.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)-thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methylphosphite, bis(2,4-di-tert-butyl-6-methylphenyl) ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighterters, flameproofing agents, antistatic agents and blowing agents.

11. Benzofuranones and indolinones, for example those disclosed in U.S. Pat. Nos. 4,325,863, 4,338,244, 5,175,312, 5,216,052, 5,252,643, DE-A-4 316 611, DE-A-4 316 622, DE-A-4 316 876, EP-A-0 589 839 or EP-A-0 591 102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]-phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

Where the compositions according to the invention are based on functional fluids, especially lubricants and hydraulic fluids and/or metalworking fluids, these liquids may likewise contain further additives which are added in order to improve specific service properties, examples being further antioxidants, metal deactivators, rest inhibitors, viscosity index improvers, pour-point depressants, dispersant/surfactants and antiwear additives. Examples of these are:

Examples of phenolic antioxidants:
These are listed under items 1.1 to 1.17 above.

Examples of aminic antioxidants:
N,N'-diisopropyl-p-phenylenediamine, N,N'-di-sec-butyl-p-phenylenediamine, N,N'-bis-(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethyl-butyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylarnine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methyl-phenyl)amino]ethane, 1,2-bis(phenylamino)propane, (o-tolyl)biguanide, bis[4-(1',3'-dimethylbutyl)phenyl]amine, tertoctylated N-phenyl-1-naphthylamine, a mixture of mono- and dialkylated tert-butyl/tertoctyldiphenylamines, a mixture of mono- and dialkylated isopropyl/isohexyldiphenylamines, mixtures of mono- and dialkylated tert-butyldiphenylamines, 2,3-dihydro-3,3-dimethyl-4H-1,4-benzothiazine, phenothiazine, N-allylphenothiazine, N,N,N',N'-tetraphenyl- 1,4-diaminobut-2-ene, N,N-bis(2,2,6,6-tetramethylpiperid-4-yl)hexamethylenediamine, bis(2,2,6,6-tetramethylpiperid-4-yl)sebacate, 2,2,6,6-tetramethylpiperidin-4-one and 2,2,6,6-tetramethylpiperidin-4-ol.

Examples of other antioxidants:
Aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,11-trithiatridecane and 2,2,15,15-tetramethyl-5,12-dihydroxy-3,7,10,14-tetrathiahexadecane.

Examples of metal deactivators, for example for copper, are:
a) Benzotriazoles and derivatives thereof, for example 4- or 5-alkylbenzotriazoles (e.g. tolutdazole) and derivatives thereof, 4,5,6,7-tetrahydrobenzotriazole and 5,5'-methylenebisbenzotriazole; Mannich bases of benzotriazole or tolutriazole, e.g. 1-[bis(2-ethylhexyl)aminomethyl)tolutriazole and 1-[bis(2-ethylhexyl)aminomethyl)benzotriazole; and alkoxyalkylbenzotriazoles such as 1-(nonyloxymethyl)benzotriazole, 1-(1-butoxyethyl)benzotriazole and 1-(1-cyclohexyloxybutyl)tolutriazole.

b) 1,2,4-Triazoles and derivatives thereof, for example 3-alkyl(or aryl)-1,2,4-triazoles, and Mannich bases of 1,2,4-triazoles, such as 1-[bis(2-ethylhexyl)aminomethyl-1,2,4-triazole; alkoxyalkyl-1,2,4-triazoles such as 1-(1-butoxyethyl)-1,2,4-triazole; and acylated 3-amino-1,2,4-triazoles.

c) Imidazole derivatives, for example 4,4'-methylenebis (2-undecyl-5-methylimidazole) and bis[(N-methyl)imidazol-2-yl]carbinol octyl ether.

d) Sulfur-containing heterocyclic compounds, for example 2-mercaptobenzothiazole, 2,5-dimercapto-1,3,4-thiadiazole and derivatives thereof; and 3,5-bis[di(2-ethylhexyl)aminomethyl]-1,3,4-thiadiazolin-2-one.

e) Amino compounds, for example salicylidenepropylenediamine, salicylaminoguanidine and salts thereof.

Examples of rust inhibitors are:
a) Organic acids, their esters, metal salts, amine salts and anhydrides, for example alkyl- and alkenylsuccinic acids and their partial esters with alcohols, diols or hydroxycarboxylic acids, partial amides of alkyl- and alkenylsuccinic acids, 4-nonylphenoxyacetic acid, alkoxy- and alkoxyethoxycarboxylic acids such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-carboxymethyl-1-dodecyl-3-methylglycerol and the amine salts thereof.

b) Nitrogen-containing compounds, for example:
I. Primary, secondary or tertiary aliphatic or cycloaliphatic amines and amine salts of organic and inorganic acids, for example oil-soluble alkylammonium carboxylates, and also 1-[N,N-bis(2-hydroxyethyl)amino]-3-(4-nonylphenoxy)propan-2-ol.
II. Heterocyclic compounds, for example: substituted imidazolines and oxazolines, and 2-heptadecenyl-1-(2-hydroxyethyl)imidazoline.

c) Phosphorus-containing compounds, for example: Amine salts of phosphoric acid partial esters or phosphonic acid partial esters, and zinc dialkyldithiophosphates.

d) Sulfur-containing compounds, for example: barium dinonyinaphthalenesulfonates, calcium petroleum sulfonates, alkylthio-substituted aliphatic carboxylic acids, esters of aliphatic 2-sulfocarboxylic acids and salts thereof.

e) Glycerol derivatives, for example: glycerol monooleate, 1-(alkylphenoxy)-3-(2-hydroxyethyl)glycerols, 1-(alkylphenoxy)-3-(2,3-dihydroxypropyl)glycerols and 2-carboxyalkyl-1,3-dialkylglycerols.

Examples of viscosity index improvers are:

Polyacrylates, polymethacrylates, vinylpyrrolidone/methacrylate copolymers, polyvinylpyrrolidones, polybutertes, olefin copolymers, styrene/acrylate copolymers and polyethers.

Examples of pour-point depressants are:

Polymethacrylate and alkylated naphthalene derivatives.

Examples of dispersants/surfactants are:

Polybutertylsuccinic amides or -imides, polybutertylphosphonic acid derivatives and basic magnesium, calcium and barium sulfonates and phenolates.

Examples of antiwear additives are:

Sulfur- and/or phosphorus- and/or halogen-containing compounds, e.g. sulfurised olefins and vegetable oils, zinc dialkyldithiophosphates, alkylated triphenyl phosphates, tritolyl phosphate, tricresyl phosphate, chlofinated paraffins, alkyl and aryl di- and trisulfides, amine salts of mono- and dialkyl phosphates, amine salts of methylphosphonic acid, diethanolaminomethyltolyltriazole, bis(2-ethylhexyl) aminomethyltolyltriazole, derivatives of 2,5-dimercapto-1, 3,4-thiadiazole, ethyl 3-[(diisopropoxyphosphinothioyl) thio]propionate, triphenyl thiophosphate (triphenylphosphorothioate), tris(alkylphenyl) phosphorothioate and mixtures thereof (for example tris (isononylphenyl)phosphorothioate), diphenyl monononylphenyl phosphorothioate, isobutylphenyl diphenyl phosphorothioate, the dodecylamine salt of 3-hydroxy-1,3-thiaphosphetane 3-oxide, trithiophosphoric acid 5,5,5-tris [isooctyl 2-acetate], derivatives of 2-mercaptobenzothiazole such as 1-[N,N-bis-(2-ethylhexyl)aminomethyl]-2-mercapto-1H-1,3-benzothiazole, and ethoxycarbonyl-5-octyldithiocarbamate.

The present invention also relates to the use of compounds of the formula I for stabilizing organic materials, especially natural or (semi)synthetic polymers or functional fluids, particularly lubricants, which are sensitive to oxidative, thermal and/or light-induced degradation. For example, the compounds are particularly highly effective as antioxidants and deposit control agents in functional fluids, as mentioned above.

Preferred compounds of the formula I, as described above, lead to preferred compositions.

One advantage of the compounds of the formula I is that, for example, when used in lubricants both an antioxidant and a deposit control action is achieved.

Since it is of tert necessary to add two or more additives to a substrate, problems may occur with solubility. This applies in particular to applications in oils and liquid polymers. The compounds according to the invention also exhibit good properties in this respect.

The compounds of the formula I are prepared, for example, in accordance with the following scheme:

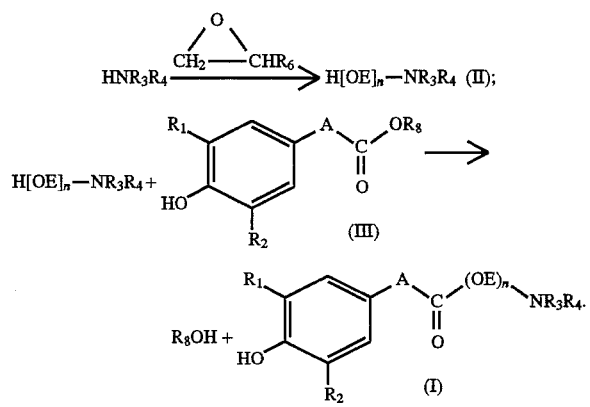

In this scheme $R_1$, $R_2$, A, E, n, $R_3$, $R_4$ and $R_6$ are the radicals already described above after the formula I and $R_8$ is H or lower alkyl, for example $C_1$–$C_4$alkyl, especially methyl.

The compounds of the formula I can be prepared, for example, by esterification or transesterification of a 4-hydroxyphenylpropionic or 4-hydroxyphenylacetic acid or ester thereof of the formula III, respectively, with a compound of the formula II, catalyzed by, for example, a Brønsted acid or, respectively, a Lewis acid [cf. Examples 1–4 below]. Other suitable catalysts besides Brønsted acids and Lewis acids are aluminium silicates, ion exchange resins, zeolites, naturally occurring phyllosilicates ("acid earths" or acid clays such as fuller's earth) or modified phyllosilicates.

Suitable Brønsted acids are mineral acids or organic acids. Suitable inorganic acids are hydrohalic acids and oxygen acids, in particular those of sulfur and of phosphorus. Examples are hydrochloric acid, sulfuric acid and phosphoric acid. Organic acids are carboxylic acids, and acids which carry organic radicals and contain sulfo and phospho groups. Examples are methanesulfonic acid, p-toluenesulfonic acid, acetic acid and propionic acid. p-Toluenesulfonic acid is particularly preferred.

Examples of suitable Lewis acids are tin tetrachloride, aluminium chloride, zinc chloride, dibutyltin oxide or boron trifluofide diethyl etherate. Dibutyltin oxide is preferred.

The (di)arylamino alcohols of the formula II are advantageously prepared by the addition of the corresponding alkylene oxides onto the (di)arylamines at temperatures which depend on the reactivity, with cooling if desired, but preferably at between 0° and 60° C., in particular between 15° and 40° C. or at about room temperature, under pressure if necessary, preferably in the presence of stoichiometric quantities of base, for example from the group consisting of the alkali metals and alkali metal organyls, such as sodium or butyllithium [described in G. A. Epling, A. Kumar, Synlett 1991/5, 347–8], or catalysed by acid, for example by the abovementioned Lewis acids such as zinc chloride or boron trifluoride diethyl etherate [described in DE 1 543 335].

The invention therefore also relates to a process for the preparation of compounds of the formula I, which comprises in a first step reacting (di)arylamines of the formula $HNR_3R_4$ with epoxides of the formula

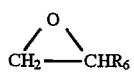

and in a second step reacting the hydroxyalkylated intermediates H[OE]$_n$—NR$_3$R$_4$ (II) with compounds of the formula

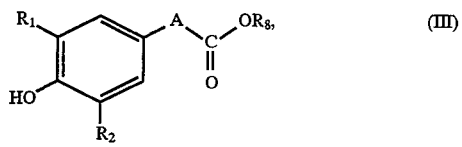

in which A, E, R$_1$, R$_2$, R$_3$, R$_4$ and R$_6$ are as already described initially after formula I, and R$_8$ is H or C$_1$-C$_4$alkyl.

When carrying out the first step of the process, the epoxide is passed, for example, into the reaction vessel, or is added, and reaction is advantageously continued until virtually none of the arylamine is left. During this time, however, a proportion of more highly hydroxyalkylated (predominantly n=2) (di)arylamino alcohol II has usually already formed. If the reaction is carried out in a closed system (autoclave), the proportion of compounds with n>1 may be higher, depending on the excess of epoxide employed.

The invention therefore also relates to mixtures of compounds of the formula I having different indices n.

Consequently, the overall reaction in the first step, depending on the degree of conversion, usually involves a molar excess of epoxide. The precise quantity of epoxide required depends on the reaction regime. Possibilities for this are batchwise operation, for example in an autoclave or at atmospheric pressure with the epoxide being passed in, or continuous operation with or without recycling of the acted epoxide. In the second step of the process, too, it is generally advantageous to have a small molar excess of alcohol, for example up to 20 mol %, in particular up to 10 mol %, based on the hydroxyphenylcarboxylic acid of the formula III or ester thereof.

When using epoxides

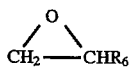

in which R$_6$ is not hydrogen (R$_6$≠H) it should be noted that the orientation of the group —E— in the (di)arylamino alcohol II and in the product I leads to two different products CE is as already described initially —CHR$_6$—CH$_2$— or —CH$_2$CHR$_6$—). The second possibility is usually by far the most predominant, and correspondingly the first variant in the examples which follow is not listed separately but is present in the corresponding products.

Step 1 can be carded out with or without solvent. It is preferred to work in a polar aprotic solvent. Examples are tetrahydrofuran (THF), dimethylformamide (DMF), dimethylacetamide (DMA), hexamethylphosphoric Iriamide (HMPTA), dimethyl sulfoxide (DMSO) and tetramethylurea (TMU), and also pyridine or alkylpyridines. A particularly preferred solvent is anhydrous DMF.

In step 2 it is likewise possible to work without solvent or diluent. However, the use of a solvent which is inert under reaction conditions is preferred. The solvent is advantageously the same as that used later on during purification.

Hydrocarbons are preferred, and toluene is particularly preferred. The solvent is also used, in particular, in order to remove by azeotropic distillation the alcohol formed.

The temperature in step 1 is advantageously from 0° to 60° C., preferably from 15° to 40° C. When fairly reactive amines are used, especially monoaromatic amines, it may be advantageous to carry out cooling. The pressure can if desired be altered but is preferably in the atmospheric range. In step 2, if desired, the alcohol formed can be stripped off under reduced pressure, and the temperature may be, for example, from 70° to 180° C., preferably from 120° to 160° C.

The mixtures which are formed during the preparation of the compounds, having various indices n and/or with various orientations of the group E, may usually be passed on for use without further purification steps. However, it is of course also possible to effect separation by customary methods such as chromatography, distillation, etc., if it is desired to obtain the pure compounds.

The examples which follow illustrate the invention in more detail without, however, limiting it. Unless otherwise specified, parts and penetrates are by weight. "t-Bu" denotes tert-butyl.

EXAMPLE 1

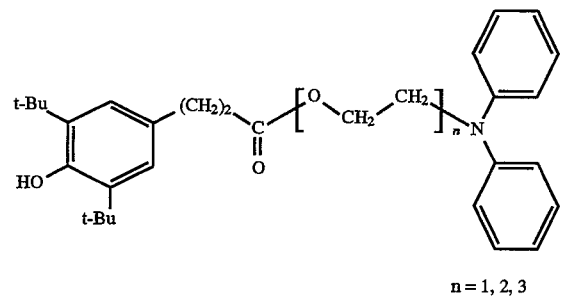

n = 1, 2, 3

8.3 g (0.36 mol) of metallic sodium are added to a solution of 52.3 g (0.31 mol) of diphenylamine in 600 ml of anhydrous dimethylformamide. After 20 min at 90° C. the sodium has reacted, and the mixture is cooled to room temperature. Ethylene oxide is passed slowly at 15°–25° C. into the brown solution until virtually no further diphenylamine can be detected by thin-layer chromatography (about 2 h). After the mixture has been cooled to 10° C. it is acidified to pH 6 with approximately 190 ml of 2N HCl. After extraction with toluene, washing of the toluene phase with water and evaporative concentration, 61.8 g of viscous brown oil are obtained which is used further dime fly.

1.4 g of dibutyltin oxide are added to a mixture of 30 g of this intermediate and 36.7 g (0.126 mol) of methyl 3-(3,5-di-tert-butyl-4-hydroxyphenyl)propionate (CA Reg. No. 6386-38-5). The methanol is slowly distilled off at 140° C. from the clear melt. Over the course of 6 h, 110 ml of toluene are added dropwise at 140° C. and are immediately distilled off together with any remaining methanol.

The brown reaction product is dissolved in 100 ml of hexane to give a clear solution which is filtered through 30 g of silica gel (toluene/hexane 1:1 to toluene) and concentrated by evaporation. 57.0 g of clear, yellow, viscous oil are obtained: $n_D^{20}$=1.5726; about 95% yield based on methyl 3-(3,5-di-tert-butyl-4-hydroxyphenyl)propionate.

According to GC analysis the product consists of 63% n=1, 23% n=2, 2.1% n=3, 5.7% diphenylamlne and 2.6% methyl 3-(3,5-di-tert-butyl-4-hydroxyphenyl)propionate.

EXAMPLE 2

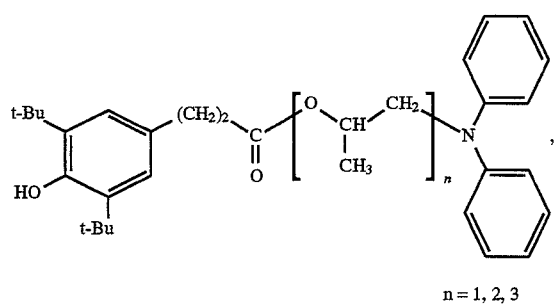

n = 1, 2, 3

2.5 g (0.11 mol) of metallic sodium are added to a solution of 17.4 g (0.10 mol) of diphenylamlne in 100 ml of anhydrous dimethylformamlde. After 30 min at 80° C. the sodium has reacted and the mixture is cooled to room temperature. Following addition of 9.8 ml of propylene oxide the temperature rises to 31° C. and stirring is continued at 40° C. for 3 h. After the mixture has been cooled to 10° C. it is acidified to pH 6 with 50 ml of 2N HCl. After extraction with toluene, washing of the toluene phase with water and evaporative concentration, 22.4 g of clear, yellow oil of moderate viscosity are obtained, which is used further directly.

1.1 g of dibutyltin oxide are added to a mixture of 22.0 g of this intermediate and 26.0 g (0.089 mol) of methyl 3-(3,5-di-tert-butyl-4-hydroxyphenyl)propionate (CA Reg. No. 6386-38-5). Over the course of 5 h 50 ml of toluene are added dropwise at 140° C. and are immediately distilled off together with the methanol formed.

The brown reaction product of moderate viscosity is diluted with a little toluene, filtered through 20 g of silica gel (toluene) and concentrated by evaporation. 42 g of clear, weakly pale yellow, viscous oil are obtained: $n_D^{20}$=1.5650; about 97% yield, based on methyl 3-(3,5-di-tert-butyl-4-hydroxyphenyl)propionate.

According to GC analysis the product consists of 77.0% n=1, 14.6% n=2, <1% n=3, 2.6% diphenylamlne and 3.0% methyl 3-(3,5-di-tert-butyl-4-hydroxyphenyl)propionate.

The compounds of Examples 3 and 4 are prepared in the manner described under Example 2, mutatis mutandis.

EXAMPLE 3

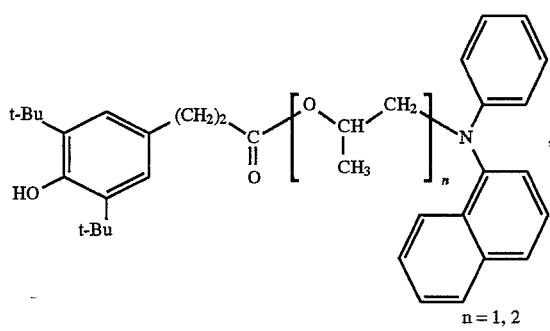

n = 1, 2

Yield: 95% based on methyl 3-(3,5-di-tert-butyl-4-hydroxyphenyl)propionate. Properties: clear, highly viscous, pale brown oil; according to GC analysis the product consists of 76.6% n=1, 14.9% n=2, 3.0% phenyl-α-naphthylamine and 3.0% methyl 3-(3,5-di-tert-butyl-4-hydroxyphenyl)propionate.

EXAMPLE 4

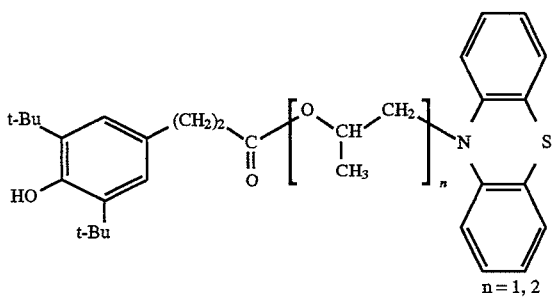

n = 1, 2

Yield: 90% based on methyl 3-(3,5-di-tert-butyl-4-hydroxyphenyl)propionate. Composition: according to TLC (silica gel/toluene and silica gel/dichloromethane)>95% n=1.

Properties: crystalline product, m.p. 130°–131° C.

EXAMPLE 5

Deposit and Oxidation Panel Test (DOPT)

This test is a variant of a test method for engine oils, especially for diesel engine oils, which was described by G. Abellaneda et al., IIIrd Symposium CEC, 1989, New Cavendish Street, London W1M 8AR, England. It is used to test the suitability of the oils with the respective stabilizer for preventing deposits on the piston.

In the test oil is dripped at a defined rate, in an oxidizing atmosphere, onto a hot, inclined metal panel to produce a film of oil. The duration of the test is 20 hours, the temperature on the metal panel is 260° C., the throughput of air is 9.7 l/h and the flow rate of the oil is 1 ml/min. The moist air atmosphere is enriched with 460 ppm of $NO_2$ and 25 ppm of $SO_2$.

After the test the metal panel is dipped in petroleum ether to remove the oil, dried, weighed and visually assessed, for example as to whether a coating has formed. The lower the weight and the visual assessment number, the better the result. The lubricating oil used is commercially available oil of API classification CD, which is diluted with the base oil STANCO 150.

The stabilizers indicated in Table I are admixed to this prepared oil in a quantity of 0.6% by weight, based on the oil, and the compositions are subjected to the DOPT test.

TABLE I

| | Deposit and Oxidation Panel Test | | |
|---|---|---|---|
| | Concentration | Deposit | |
| Product of Example | [% by weight] | weight [mg] | visual |
| 2 | 0.6 | 6 | 2 |
| 4 | 0.6 | 4 | 0 |
| none added | — | 72 | 14 |

I claim:

1. A compound of the formula I $$\text{(I)}$$

in which $R_1$ and $R_2$ are independently of one another $C_1-C_{20}$alkyl, allyl, methallyl, unsubstituted or $C_1-C_8$alkyl-substituted $C_5-C_{12}$cycloalkyl, $C_5-C_8$cycloalkenyl, phenyl, or $C_7-C_9$phenylalkyl, A is a direct bond, —CH$_2$—, —(CH$_2$)$_2$— or —CH$_2$—CH(CH$_3$)—, E is —(CH$_2$)$_2$—, —CHR$_6$—CH$_2$ or —CH$_2$CHR$_6$—, n is 1, 2 or 3

$R_3$ is phenyl, naphthyl, $C_7-C_9$phenylalkyl, $C_7-C_{18}$alkylphenyl or is of the formula $R_4$ is phenyl, naphthyl, $C_7-C_9$phenylalkyl, $C_7-C_{18}$alkylphenyl or is a radical of the formula or $NR_3R_4$ is a group of the formula $NR_3R_4$ is a group of the formula $R_5$ is hydrogen, $C_1-C_{18}$alkyl, allyl, methallyl, unsubstituted or $C_1-C_8$alkyl-substituted $C_5-C_{12}$cycloalkyl, phenyl or naphthyl, $R_6$ is hydrogen, $C_1-C_{20}$alkyl or $C_2-C_{20}$alkyl which is interrupted by —O—, —S—, —NR$_7$— or —C(O)O—, and $R_7$ is hydrogen or $C_1-C_6$alkyl.

2. A compound of the formula I according to claim 1, in which $R_1$ and $R_2$ are independently of one another $C_1-C_8$alkyl, $C_5-C_8$cycloalkyl or $C_7-C_9$phenylalkyl, A is —(CH$_2$)$_2$— or —CH$_2$—CH(CH$_3$)—, n is 1 or 2, $R_3$ and $R_4$ are independently of one another phenyl, naphthyl, $C_7-C_9$phenylalkyl or $C_7-C_{18}$alkylphenyl, or $NR_3R_4$ is a group of the formula or $R_5$ is hydrogen, $C_1-C_8$alkyl or phenyl, and $R_6$ is hydrogen, $C_1-C_{20}$alkyl or $C_2-C_{20}$alkyl which is interrupted by —O— or —S—.

3. A compound according to claim 2, in which $R_1$ and $R_2$ independently of one another are $C_1-C_5$alkyl, $C_5-C_6$cycloalkyl or $C_7-C_9$phenylalkyl, n is 1, $R_3$ and $R_4$ are independently of one another phenyl, naphthyl, $C_7-C_9$phenylalkyl or $C_7-C_{18}$alkylphenyl, or $NR_3R_4$ is a group of the formula and
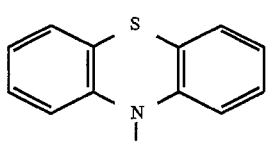
and
$R_6$ is hydrogen or $C_1$–$C_4$alkyl.
4. A compound according to claim 1 of the formula
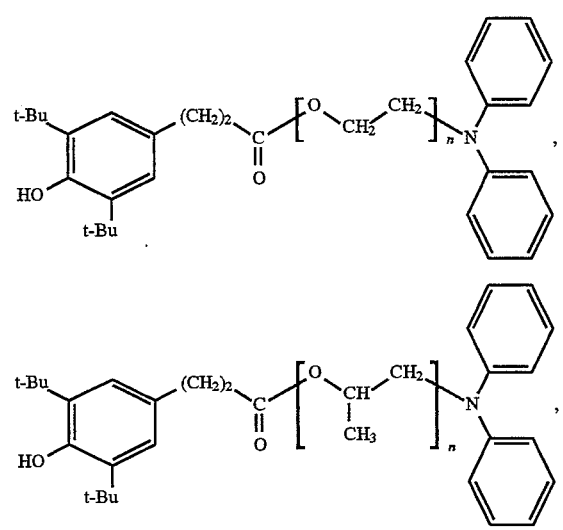
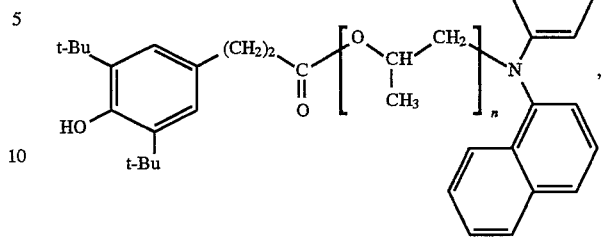
or
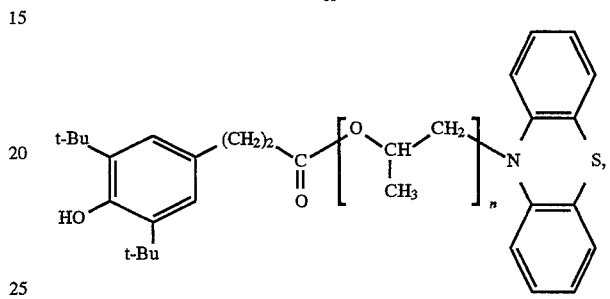
in which
n is 1, 2 or 3 and t-Bu is the abbreviation of tert-butyl.
* * * * *